United States Patent [19]

Vaillancourt

[11] Patent Number: 4,585,435
[45] Date of Patent: Apr. 29, 1986

[54] EXTENSION SET FOR DRUG DELIVERY

[75] Inventor: Vincent L. Vaillancourt, Livingston, N.J.

[73] Assignee: The Telescope Folding Furniture Co., Inc., Granville, N.Y.

[21] Appl. No.: 615,594

[22] Filed: May 31, 1984

[51] Int. Cl.$^4$ ............................................... A61M 1/00
[52] U.S. Cl. ..................................... 604/27; 604/44; 604/284
[58] Field of Search .............. 604/257, 258, 283, 284, 604/252, 272, 27, 44, 43

[56] References Cited

U.S. PATENT DOCUMENTS

| | | | |
|---|---|---|---|
| 3,916,892 | 11/1975 | Latham, Jr. ................... | 604/272 X |
| 3,970,490 | 7/1976 | Raines et al. ....................... | 604/252 |
| 4,099,528 | 7/1978 | Sorenson et al. ..................... | 604/44 |
| 4,333,455 | 6/1982 | Bodicky .............................. | 604/284 |
| 4,385,631 | 5/1983 | Uthmann ............................. | 604/284 |

Primary Examiner—John D. Yasko
Attorney, Agent, or Firm—Kenyon & Kenyon

[57] ABSTRACT

The extension set has two lumen for conveying an intravenous liquid and a drug through a common connector to a catheter for direct infusion of the drug to a patient. The lumen are connected in common to the connector or may be separated by a partition wall. In other embodiments, the drug carrying lumen can be disposed within the intravenous tube and may be of micro-bore size.

25 Claims, 10 Drawing Figures

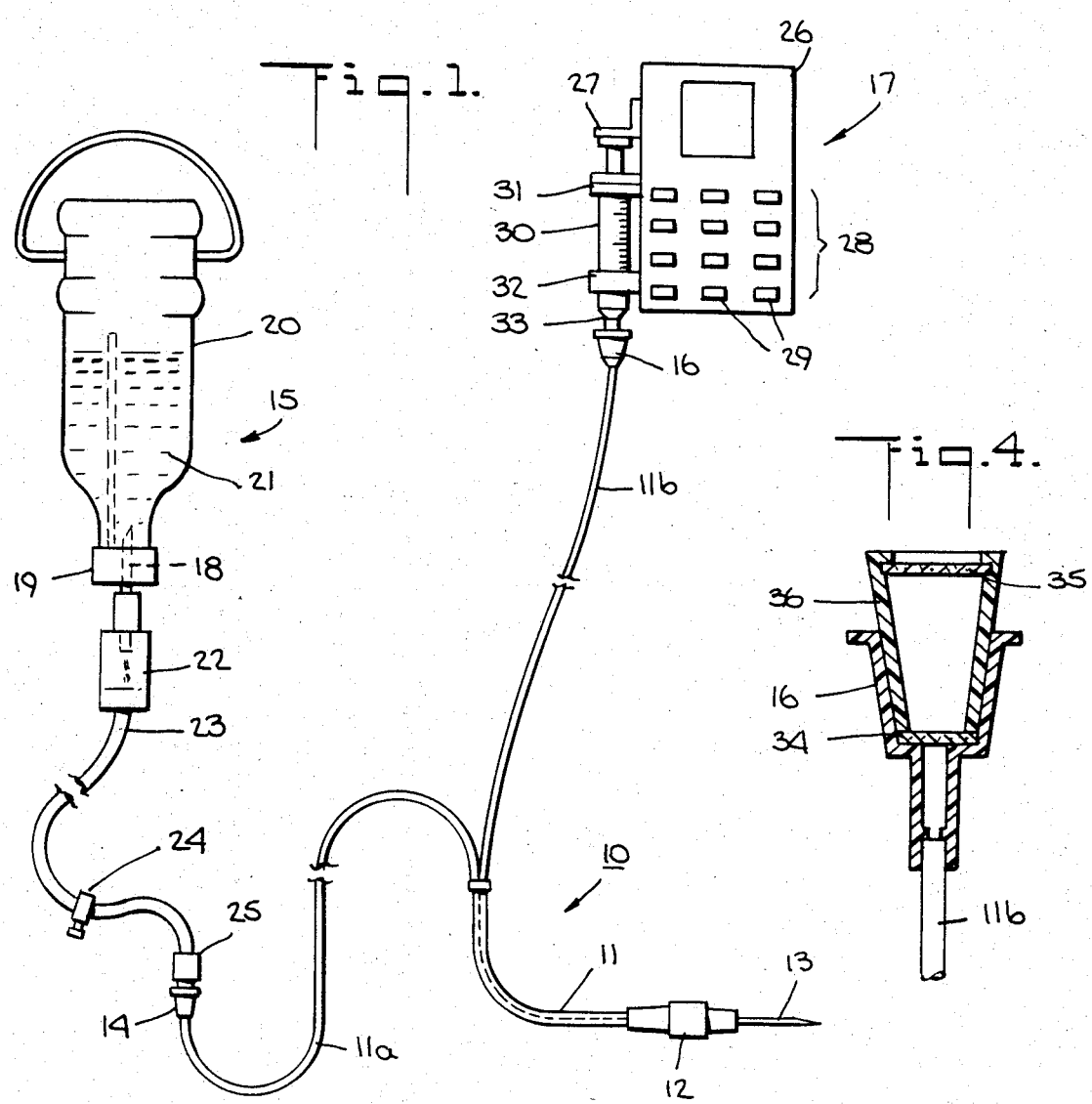
Fig. 1.
Fig. 4.
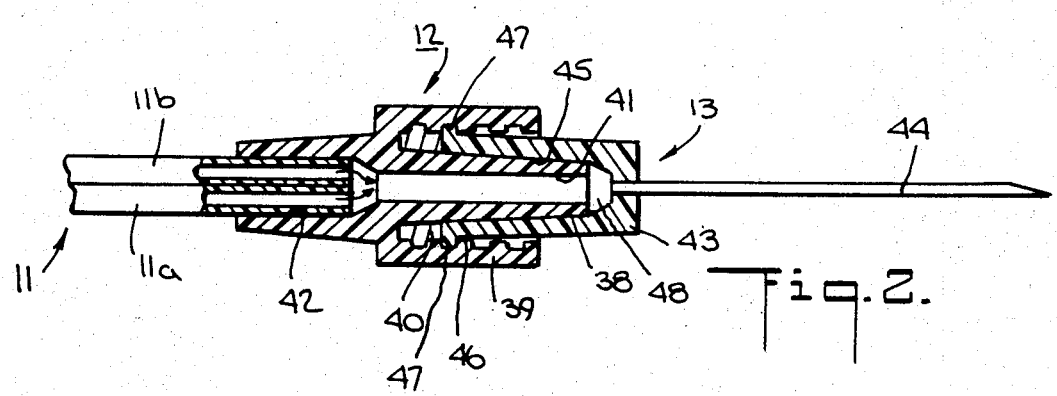
Fig. 2.
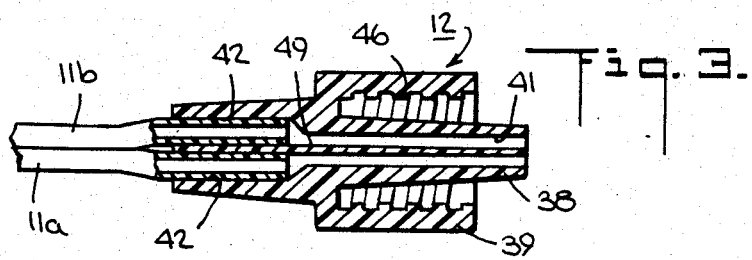
Fig. 3.

EXTENSION SET FOR DRUG DELIVERY

This invention relates to an extension set for drug delivery. More particularly, this invention relates to a method of administering a drug.

As is known, various types of systems are known for feeding fluids into a patient intravenously. Various systems are also known wherein drugs or the like can be added to an intravenous solution which is being administered to a patient. For example, it has been known to connect an infusion tube to a Y-connection having branches which are, in turn, connected to two separate tubes, one of which leads to a source of intravenous solution while the other leads to a drug source. In these cases, a drug can be added from time-to-time by being mixed in with the intravenous solution. Examples of such systems are described in U.S. Pat. Nos. 2,866,457; 4,105,029; 4,114,617; and 4,335,717.

Other similar systems have also been known wherein a drug can be administered via a sealed branch line joined to a conduit by a rubber tube, such as described in U.S. Pat. No. 2,656,835. In this case, use is made of a hypodermic syringe to pierce a self-sealing means at the end of the branch tube in order to be able to introduce a drug.

Several problems have, however, been associated with systems of the above types of drug administration. For example, several publications have indicated that certain drugs adsorb to glass, to plastic infusion systems or to filtration materials, thus potentially decreasing the amount of drug ultimately delivered to a patient. Particular problems have also been noted with such types of systems in the administration of drugs to small pediatric patients in that the amount of time for completion of a drug infusion, once begun, is frequently unduly prolonged and also not consistent with the time predicted to be required to deliver the prescribed drug dosage. In this regard, reference is made to Gould and Roberts, *The Journal of Pediatrics,* September 1979, pages 465–471; Leff and Roberts, *The Journal of Pediatrics,* April 1981, pages 631–635; and Roberts, "Intravenous Administration of Medication in Pediatric Patients: Problems and Solutions", *Pediatric Clinics of North America,* February 1981, pages 23–24.

It is also known that when a drug is introduced via an intravenous line with such heretofore known systems, that the administration of the drug follows a "peak and valley" pattern with a pronounced "spike" at some point during administration. That is, when the drug is first introduced into a parallel line or shunt connection, there is a "hold-up" of the drug before reaching the intravenous fluid and thereafter, there is a varying dilution of the drug while passing with the intravenous fluid into the patient. As a result, there may be some initial spike in the administration of the drug followed by a tailing off of the actual amounts being infused, and the intended dosage and the intended rate and time of the dosage may not be achieved.

Aside from the above problems, it has also been known that the infusion of a small amount of air into a patient may be quite damaging if not fatal. This is particularly so in the case of small pediatric patients. Hence, there is a need to eliminate any air in an administration set for infusing liquids and drugs into a patient. In the past, it has been necessary for a nurse or other qualified person to manipulate the administration set in order to prime the set while expelling any air therefrom. In this regard, the air is generally detected by the appearance of small bubbles. In any event, cumbersome procedures are frequently required in order to insure that all the air has been eliminated from the administration set.

Accordingly, it is an object of this invention to provide a relatively simple technique for intravenously delivering drugs to a patient.

It is another object of the invention to accurately inject a drug into a patient in proper dosages.

It is another object of the invention to provide a relatively simple extension set which can be self-priming.

It is another object of the invention to provide an extension set which insures delivery of a proper drug dosage to a patient.

It is another object of the invention to deliver a drug intravenously to a patient accurately in terms of dosage, rate and time.

Briefly, the invention provides an extension set for delivering a drug to a patient which comprises means defining at least two lumen and a common connector. In this regard, each lumen has an open distal end and a terminal end, with one lumen sized to convey an intravenous fluid to the terminal end thereof while the other lumen is sized to convey a drug to the terminal end thereof. The connector is constructed to receive the terminal end of each lumen and has means at one end for connecting to a catheter in order to deliver the intravenous fluid and the drug thereto.

In one embodiment, the connector is provided with an interfacing chamber of relatively short dimensions for receiving each terminal end of the lumen in order to interface the conveyed drug with the intravenous fluid immediately prior to passage into the catheter.

In another embodiment, the connector is provided with a pair of sockets for individually receiving two lumen and a partition wall which extends between the sockets to the means at the end of the connector for connecting to the catheter.

In the case where the extension set is to be used for small pediatric patients, the two lumen are each of micro-size with an internal diameter of 0.020 inches.

In still other embodiments, the means defining the lumen is in the form of two tubes each of which defines a lumen and with one tube disposed within the other tube. In addition, the innermost tube may be movably mounted in the outer tube and slidably mounted in the connector in order to project from the connector. In this embodiment, the inner tube can be used to deliver a drug directly into a vein of a patient.

In order to provide for self-priming of the extension set, the drug conveying lumen is provided with a hydrophilic filter at the distal end so as to prevent passage of air into the tube. In addition, a hydrophobic filter may also be removably attached at the distal end in order to prevent liquid from passing out of or into the drug conveying lumen when not in use.

The extension set may be connected via the connector to any suitable catheter which can be implanted into a patient, such as a small pediatric patient, an adult, or an animal. In addition, each of the lumen of the set may be respectively connected to a means for delivering an intravenous fluid or a means for delivering a drug. In this regard, a double-tube lumen can be used to define the two lumen wherein the double-tube lumen can be separated along a common joint to accommodate to different locations of the fluid source and the drug source. A slidable collar may also be positioned to retain the remainder of the lumen in side-by-side relation.

The invention also provides a method of administering a drug wherein the hold-up time is minimized if not eliminated. In this regard, the method comprises the steps of connecting a first lumen of an extension set to a catheter implanted intravenously in a patient in order to deliver a flow of intravenous fluid to the patient at a predetermined rate over a period of time, and of introducing a drug at a predetermined rate and dosage for an incremental time through a second lumen of the extension set directly into the patient through the catheter.

In one embodiment, the drug can be interfaced with the fluid flow immediately upstream of the catheter in an interfacing chamber which is of a volume to contain, for example, no more than two drops of the drug. In another embodiment, the drug can be introduced through the catheter without dilution with the fluid flow.

In accordance with the method, the drug can be delivered to the extension set catheter connection from a remote source, for example via a syringe pump.

Since the method permits a substantially direct infusion of drug into the catheter, substantially precise dosages, rates and times of delivery can be suitably programmed in an automatic manner at spaced-apart intervals of time.

In the case of an extension set having two lumen disposed in side-by-side relation, the invention provides a simple method of clearing the extension set of air. In this respect, a fluid is first delivered under pressure through one lumen and via the connector into the second drug conveying lumen. During this time, air is vented from the drug conveying lumen through the hydrophilic filter and a removable hydrophobic filter at the distal end. Delivery of the fluid is then terminated in response to fluid appearing at the hydrophobic filter. During this self-priming operation, the connector of the extension set is closed off by a suitable vent cap. Further, air can be detected within the lumen since any air should appear as small bubbles. With the lumen and connector being made of suitable transparent material, the user should be able to readily see any bubbles.

These and other objects and advantages of the invention will become more apparent from the following detailed description taken in conjunction with the accompanying drawings wherein:

FIG. 1 illustrates a schematic view of an extension set in accordance with the invention employed with an administration set;

FIG. 2 illustrates a cross-sectional view of a connector and the terminal ends of a pair of lumen of the extension set of FIG. 1;

FIG. 3 illustrates a view similar to FIG. 2 of a modified connector in accordance with the invention;

FIG. 4 illustrates a cross-sectional view of a terminal end of a drug delivery lumen prior to hook-up;

Figure 5:
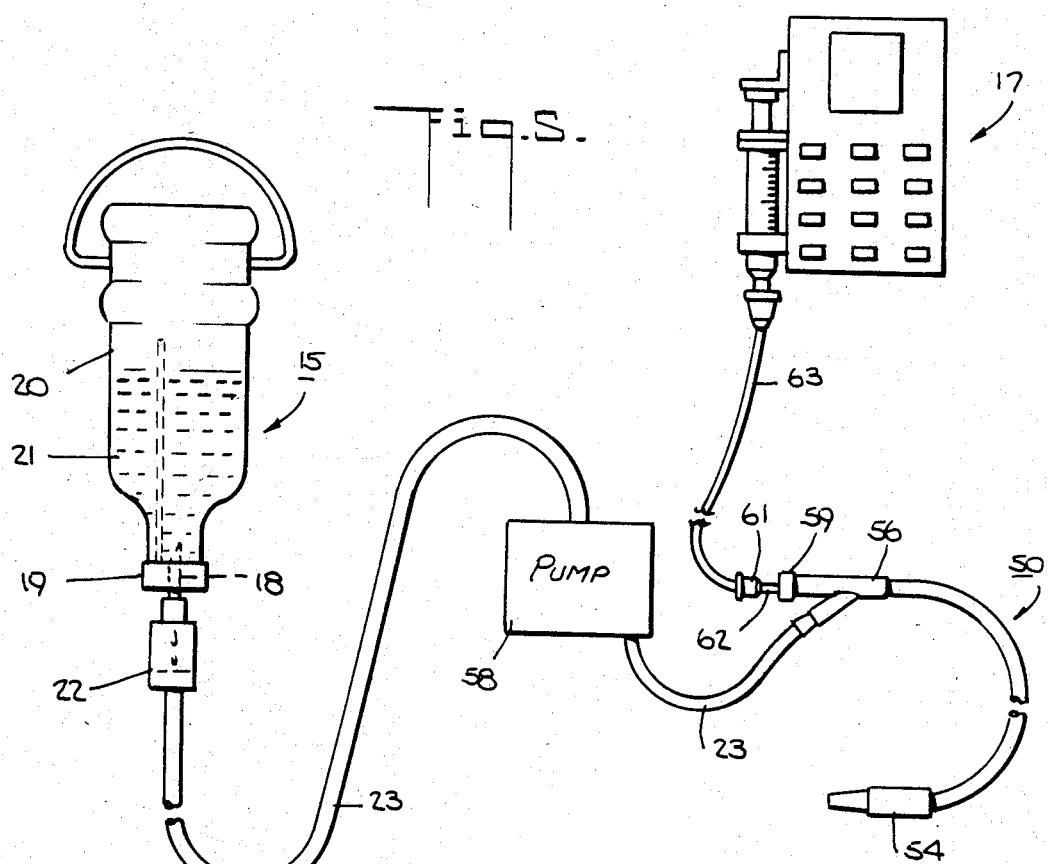
FIG. 5 illustrates a modified extension set in accordance with the invention having a tube-in-tube construction.

Referring to FIG. 1, the extension set 10 includes a double-tube lumen 11 and a catheter connector 12. The connector 12 is removably secured to a catheter 13 while one arm 11a of the double-tube lumen 11 is connected via a connector 14 to a means such as an administration set 15 for delivering an intravenous fluid and the other arm 11b of the double-tube lumen 11 is connected via a connector 16 to a means such as a syringe pump 17 for delivering a drug.

The double-tube lumen 11 is made of a plastic extrusion which has a pair of lumen (i.e., passageways or openings) through which fluids may be conveyed. The extension is such as to be separable as by stripping into the two arms 11a, 11b with each arm containing a respective lumen.

The administration set 15 is of conventional construction and includes a piercing spike 18 which passes through a rubber bung 19 of an intravenous solution bottle 20 containing intravenous fluid 21, a drip meter 22, a delivery tube 23, a flow control clamp 24 about the tube 23 and a male luer connector 25 for connection to the connector 14 of the extension set 10.

The syringe pump 17 is of conventional construction and includes a housing 26 which houses a suitable motor and power supply, e.g., batteries, a movable driver 27, and suitable electronic program means 28 having buttons 29 on the face of the housing 26 for moving the driver 27. In addition, a syringe 30 containing a supply of drug is removably mounted on the side of the housing 26 under the driver 27 via a fixed bracket 31 and a resilient clip 32. The syringe 30 includes a suitable outlet 33 such as a male luer connector for removable connection to the connector 16 of the extension set 10.

Referring to FIG. 4, the connector 16 contains a hydrophilic filter 34 to prevent an inflow of air into the lumen 11b. A hydrophobic filter 35 which is disposed in a housing 36 is also removably mounted in the connector 16 when the connector 16 is not connected to the syringe pump 17. The hydrophilic filter 34 serves to prevent air from passing into the lumen 11b while the hydrophobic filter 35 prevents fluid from passing therethrough.

Referring to FIG. 1, the arms 11a, 11b are removably secured together in a side-by-side relationship. In this respect the structure of the tube 11 may be such that the arms 11a, 11b can be pulled apart under the application of a small manually applied force, for example into the disposition as shown in FIG. 1. Further, the extension set 10 is provided with a collar 37 which envelops the arms 11a, 11b and which can be slid along the tube 11 to a junction point at which the arms 11a, 11b separate from one another.

Referring to FIG. 2, the connector 12 is of a male luer type having a centrally disposed male part 38 with a conical outer surface and a surrounding wall 39 which defines a recess 40 with the male part 38. In addition, a bore 41 extends through the connector 12 from one end to the other. At the end opposite the male part 38, the connector 12 is provided with a socket 42 of greater cross-sectional area than said bore to slidably receive the terminal end of the tube 11. Any suitable means may be used to fixably secure the terminal end of the tube 11 in the socket 42. As indicated, the bore 41 extends from the socket 42 and is coaxially spaced from the double tube lumen 11 to receive a delivered intravenous fluid and drug therefrom.

The catheter 13 includes a female mounting adaptor 43 and a needle or plastic cannula 44 of known construction. As indicated, the mounting adaptor 43 has an internal bore 45 which is conically tapered so as to mate with the male part 38 of the connector 12. In addition, the wall 39 of the connector 12 is provided with a thread 46 to engage with a pair of arcuate wings 47 on the adaptor 43 in a thread-like connection so as to fix the adaptor 43 to the connector 12 against axial movement as is known.

The needle 44 extends from the adaptor 43 in coaxial manner with the adaptor 43 to an injection site in a patient.

As indicated in FIG. 2, an interfacing chamber 48 is defined within the connector 12 from the terminal end of the tube 11 up to the needle 44. Hence, during use, a drug which is delivered via the lumen 11b will be exposed to the intravenous fluid delivered by the lumen 11a prior to entry into the needle 44. However, the length of this interfacing chamber 48 is relatively small and does not permit significant mixing of the drug with the intravenous fluid. For example, the volume of such a chamber 48 may be such as to contain no more than two drops of the delivered drug.

Referring to FIG. 3, wherein like reference characters indicate like parts as above, in order to preclude interfacing of a delivered drug with the intravenous fluid, the connector 12 can be provided with a pair of sockets 42 with each receiving a respective lumen 11a, 11b as well as with a partition wall 49 which is located between the sockets 42 and which extends to the end of the male part 38. In this embodiment, no interfacing chamber is formed in the connector 12. Of note, a double-lumen catheter (not shown) may also be connected to the connector 12.

The construction of the extension set 10 is such that a drug can be delivered in a predetermined dosage, at a predetermined rate and over a predetermined increment of time directly into a patient. As such, there is no hold-up time, practically speaking, of the drug within the extension set 10.

In order to utilize the extension set 10, for example to self-prime the set, a suitable closure cap (not shown) is placed over male part 38 of the connector 12. Thereafter, with the lumen 11b unplugged from the pump 17, the intravenous fluid 21 can be delivered into the lumen 11a, for example under pressure or under gravity. Upon reaching the connector 12, the intravenous fluid would then flow into the terminal end of the lumen 11b and flow to the distal end. During this time, any air which is in the lumen 11b can be vented through the filters 34, 35 (see FIG. 4) to the atmosphere. When fluid reaches the hydrophilic filter 34, and continues to the hydrophobic filter 35. Since a hydrophobic filter will not pass fluid, the fluid flow stops and the set is primed. Should a negative pressure develope in the lumen 11b, fluid will not leave the lumen 11b since the hydrophilic filter 34 will not pass air once the filter 34 has "wet out". The hydrophobic filter 35 with or without the hydrophobic filter 34 can then be removed and the connector 16 plugged into the connector 33 of the syringe 30 and the closure cap removed from the connector 12. The connector 12 can then be fixed to the catheter 13.

After implanting the needle 14 into the vein of a patient such as a small pediatric patient, adult or animal, the drip meter 22 can be controlled so as to deliver the intraveneous fluid 21 intraveneously to the patient. Thereafter, when a drug is to be administered, the pump 17 is actuated, for example, via the control means 28 and the drug delivered in predetermined doses.

For example, wherein the syringe 30 contains a supply of drug of, e.g., two cubic centimeters to fifty cubic centimeters, the driver 27 can be programmed to move over a distance and for a time to infuse a predetermined dosage at a predetermined rate for a predetermined time. Of note, the pump 17 can be provided with a suitable print-out mechanism so as to check a programmed drug delivery against a label on a delivered syringe containing a prescription for the administration of a drug.

By way of example, where the extension set 10 is to be used for pediatric patients, the drug delivery lumen 11b may have an internal diameter of 0.020 inches or another suitable microsize. The intravenous lumen 11b may be of the same internal diameter. In the case of an adult patient, the intravenous lumen 11b may be of an internal diameter of 0.100 inches.

Figure 6:
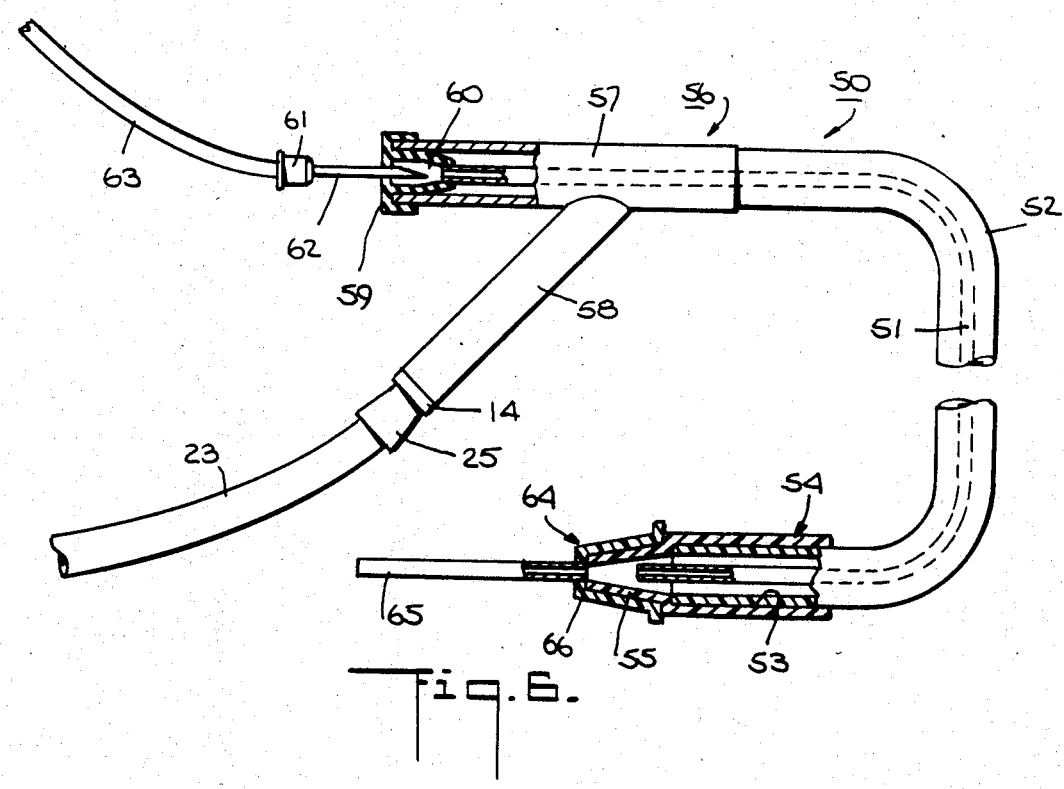
FIG. 6 illustrates an enlarged partly cross-sectional view of the extension set of FIG. 5.

Referring to FIG. 5 wherein like reference characters indicate like parts as above, the extension set 50 is constructed so that the means defining a pair of lumen is in the form of a pair of elongated flexible tubes 51, 52 which are disposed substantially one within the other. As illustrated in FIG. 6, the outermost tube 52 has a terminal end which is secured within a socket 53 of a luer slip connector 54 whereas the inner tube 51 extends through the socket 53 into a tapered male part 55 of the connector 54. In addition, a Y-connector 56 is connected at the distal end to the tube 52. This connector 56 has one arm 57 which receives the two tubes 51, 52 in concentric relation and a second arm 58 which communicates with the interior of the outer tube 52 so as to deliver a fluid from an administration set 15 via (a pump) 58 and delivery tube 23 as indicated in FIG. 5.

In addition, the Y-connector 56 has a needle connection 59 in the form of a rubber diaphragm which serves as an intermittent injection site. As indicated, a well 60 is disposed within the rubber diaphragm 59 and is reduced in section until terminating in a small opening which receives the inner tube 51. In addition, a syringe 61 having a needle 62 is utilized to pierce the rubber diaphragm 59 so as to deliver a drug thereto, for example from a suitable syringe pump 17 via a supply line 63 as indicated in FIG. 5.

As shown in FIG. 6, a catheter 64 may be of modified construction with a needle 65 and an adaptor 66 of conical shape which fits over the male part 55 of the connector 54 in known manner.

As indicated in FIG. 6, the inner tube 51 is of smaller size than the outer tube 52, for example, the inner tube 51 is of micro-bore size.

The extension set 50 operates so that a drug may be directly delivered to the catheter 64 through the micro-bore tube 51 with virtually no hold-up time or dilution within the outer tube 52. Since the micro-bore tube 51 occupies an almost insignificant amount of space within the outer tube 52, the normal extension set priming times, flow rates and pressure drops are affected to an almost negligible degree.

Figure 7:
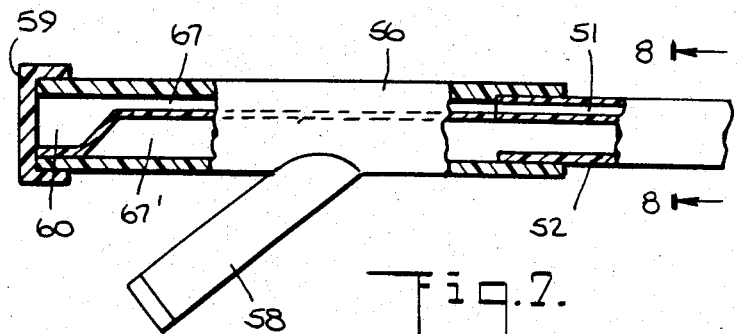
FIG. 7 illustrates a modified construction of an extension set in accordance with the invention.
Figure 8:
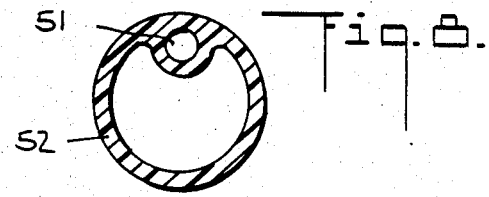
FIG. 8 illustrates a view taken on line 8—8 of FIG. 7.

Referring to FIGS. 7 and 8, wherein like reference characters indicate like parts as above, the micro-tube 51 may be made as part of the wall of a double tube extrusion. In this case, the need to position the micro-bore tube 57 within the infusion tube 52 is eliminated. Further, the Y-connector 56 is molded with a pair of channels 67, 67' to communicate with the respective tubes or lumen 51, 52.

Figure 9:
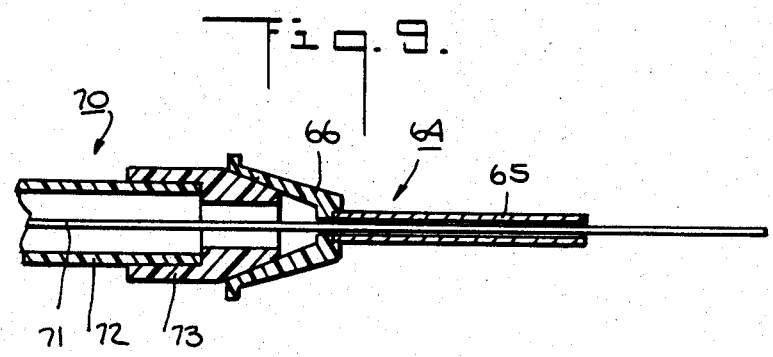
FIG. 9 illustrates a further modified construction in accordance with the invention.

Referring to FIG. 9, wherein like reference characters indicate like parts as above, an extension set 70 may be constructed with a drug carrying tube 71 within an intravenous tube 72 in a manner similar similar to that described above with respect to FIG. 6 and with the inner tube 71 movably mounted within the outer tube 72. In addition, with the outer tube 72 fixably secured in a connector 73, the inner tube 71 may be movably or slidably mounted within the connector 73 to extend through the needle 65 of the catheter 64. With a suitable means connected to the outer tube 72 at an upstream point, the inner tube 71 can be slid out of the needle 65 to a greater or lesser extent so as to deliver a drug directly into the vein of a patient. The means for moving the outer tube 72 may employ an accordian-like section (not shown) on the outer tube 72 so that the outer tube 72 can be collapsed somewhat permitting the inner tube 71 to extend through the adaptor 73 and catheter 64.

Figure 10:
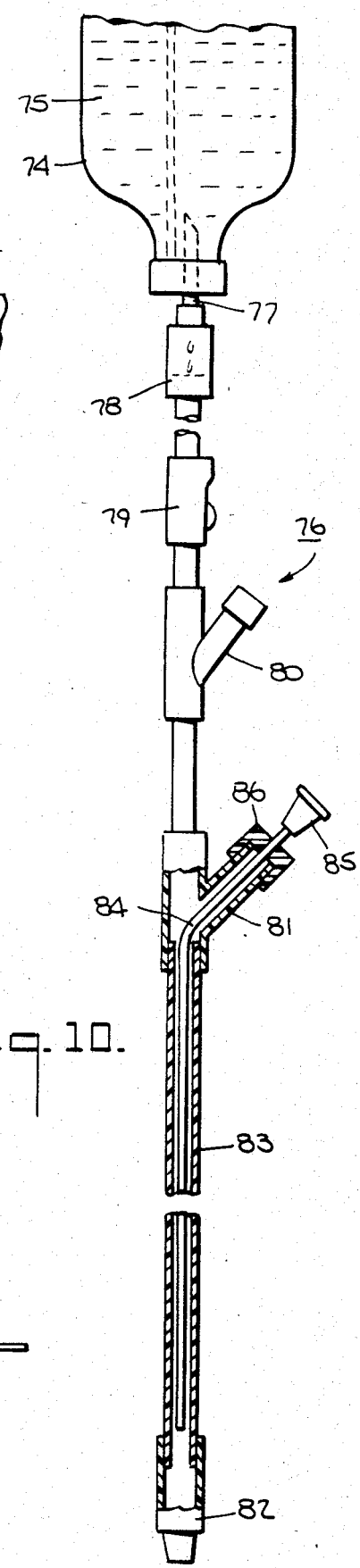
FIG. 10 illustrates an extension set similar to that of FIG. 5.

Referring to FIG. 10, for purposes of experiment, an extension set was constructed in a manner as illustrated. In this case, an intravenous (IV) infusion system was set up with a solution bottle 74 which contained sterile distilled water 75 and an administration set 76 which was connected to a rubber bung (not shown) of the solution bottle. The system also included a piercing spike 77, a drip chamber 78, a flow control clamp 79, a pair of Y-connectors 80, 81 and a male luer adaptor 82 separated from the lower connector 81 by a seven and one half inch length of IV tubing 83. Of note, the upper connection 80 was not used in the tests.

Three separate sets of test solutions were prepared to simulate fluids where were equivalent to the primary solution and heavier and lighter in specific gravity than the primary solution These solutions were:

(1) distilled water containing a green coloring dye,
(2) a solution of 70% isopropyl alcohol in water containing a blue food-coloring dye, and
(3) a solution of 20% sugar in water containing a red food-coloring dye.

After setting up the IV infusion system as shown in FIG. 10 but without the inner tube 83 (TEST CONFIGURATION I), the flow rate of the primary solution was adjusted using the flow control clamp 79 to obtain the desired flow rate. Test solutions were injected into the Y-connector 81 using a 2 cc plastic syringe and 20 Ga. hypodermic needle. The time required for the color to disappear at the downstream male adaptor 82 was obtained and recorded.

The IV infusion system was modified to include a length of micro-bore tube 84 of 0.05 inch OD×0.013 inch ID., and a luer adaptor 85 was inserted into the tube through a rubber cap 86. The micro-bore tube 84 terminated at the downstream male luer adaptor 82. After adjusting the flow control clamp 79 to the desired flow rate for the primary solution, test solutions were introduced into the system through the micro-bore tube 84. This was accomplished by filling 2 cc plastic syringes with test solutions and connecting them to the micro-bore tube 84 adaptor. Test solutions were injected from the syringes into the system. The time for color to disappear at the base of the luer adaptor 82 was observed and recorded (TEST CONFIGURATION II).

To observe the effect of gravity on the infusion time for the various test solutions, the tubing below the Y-connector 81 was positioned such that the male luer adaptor 82 was located at the same height as the connector 81. This had the effect of creating a low spot in the tubing very much like that which would occur when the IV line was placed on a patient. After running test solutions through the micro-bore tube, the tube was removed prior to injecting test solutions directly into the IV line (TEST CONFIGURATION III).

To observe the effect of gravity on light (low specific gravity) solutions, the male luer adaptor 82 was positioned vertically with the outlet at the highest point, (TEST CONFIGURATION IV).

To determine the effect of venous pressure on the IV infusion system, a 24 Ga. 1¼ inch Teflon catheter was connected to the outlet male luer adaptor 82. The Telfon catheter tip was placed horizontally siz inches under water. The time for color (from the test solutions) to disappear at the male luer adaptor was observed and recorded. (TEST CONFIGURATION V).

This procedure was repeated using micro-bore tubing. (TEST CONFIGURATION VI).

TEST RESULTS

The following Table 1 summarizes the experimental results obtained:

TABLE 1

| TEST CONFIG-URATION | PRIMARY SOLUTION FLOW RATE CC/MIN. | FLUID IN-JECTED | TIME TO LEAVE IV SYSTEM | |
|---|---|---|---|---|
| | | | PREDICTED | ACTUAL |
| I | 1 | Water | 1 min. 22 sec. | 8 min. 45 sec. |
| I | 1 | Sugar | 1 min. 22 sec. | 2 min. 27 sec. |
| I | 1 | Alcohol | 1 min. 22 sec. | 20 min. |
| I | 2 | Water | 42 sec. | 4 min. |
| I | 2 | Sugar | 42 sec. | 2 min. 17 sec. |
| I | 2 | Alcohol | 42 sec. | >20 min. |
| II | 1 | Water | | 35 sec. |
| II | 1 | Sugar | | 20 sec. |
| II | 1 | Alcohol | | 1 min. 35 sec. |
| II | 2 | water | | 20 sec. |
| II | 2 | Sugar | | 8 sec. |
| II | 2 | Alcohol | | 50 sec. |
| III | 1 | Sugar | 1 min. 24 sec. | 55 min. |
| III | 2 | Sugar | 42 sec. | 45 min. |
| III | 6 | Sugar | 14 sec. | 6 min. |
| IV | 1 | Alcohol | | 18 sec. |
| IV | 2 | Alcohol | | 10 sec. |
| V | 2 | Water | 42 sec. | 4 min. 10 sec. |
| V | 2 | Sugar | 42 sec. | 2 min. 12 sec. |
| V | 2 | Alcohol | 42 sec. | 20 min. |
| VI | 2 | Water | | 18 sec. |
| VI | 2 | Sugar | | 10 sec. |
| VI | 2 | Alcohol | | 45 sec. |

Results obtained indicated differences between actual and predicted drug infusion time vary by a minimum factor of two and maybe sixty or higher.

The use of micro-bore tubing within the IV infusion line ending at the male luer adaptor which connects to the patient's catheter resulted in substantially reduced drug residence within the IV infusion line.

In the initial experiments in which the administration set was held in the vertical position, clearance times for sugar solutions were significantly lower than for alcohol solutions. When a slight rise (one inch) was introduced into the tubing set downstream from the injection site, the sugar solution clearance time substantially increased.

In all experiments performed, the use of a micro-bore tube resulted in a minimum one order of magnitude difference in clearance time when compared to test solutions injected directly into the IV line.

After injection of test solutions, the clearance time for both sugar and water was very rapid. Clearance time for alcohol solutions was somewhat longer. However, when the male luer adaptor of Test Configuration II was inverted such that the outlet faced up, the clearance time for alcohol solutions dramatically dropped. This effect is due to the alcohol solution having a lower specific gravity than the primary solution.

Various modifications may be made in the extension sets. For example, in order to feed two drugs continuously or intermittently to a patient, two micro-bore tubes can be used. This would eliminate the potential of in-line incompatability, for example where one drug might precipitate in the presence of the other drug, while providing for the patient to receive both drugs simultaneously.

The drug conveying tube can be made of any suitable material, for example polyethylene, Teflon, or other non-absorbing or non-reacting plastic. Further, the drug conveying tube or lumen may be made from an opaque plastic such as barium sulfate filled Teflon to allow the infusion of light sensitive drugs. Further, in order to inject a series of drugs, for example followed by a "chaser" such as water or a normal saline solution, a multi-lumen connector can be used at a Y-connector.

The invention thus provides an extension set which is capable of infusing a drug directly into a patient with little or no hold-up time. Further, a drug can be administered at a predetermined dosage, a predetermined rate and over a predetermined interval of time.

Further, the invention provides an extension set which can be readily used in a simple reliable manner.

Still further, in the case where the extension set is of the self-priming type as illustrated in FIGS. 1 to 4, bubbles of air can be eliminated in the extension set so as to permit use in delicate situations, for example for premature pediatric patients.

In any of the above-described embodiments, the hydrophilic filter may be bacteria retentive, e.g., with a pore size small enough to prevent bacteria from passing through. Thus, the extension set can be characterized as a closed system, i.e., a system which during hook-up to a drug syringe pump will not allow bacteria to enter.

Of note, the structure as shown for example in FIG. 9 may be used to withdraw blood without the need for stopcocks and drawing blood thru the primary line in such applications as invasive blood pressure monitoring and conventional IV administrations hook-up. For the case of invasive blood pressure monitoring there would be no need to shut the system down as is currently done nor would there be any danger of clogging the primary line as sometimes occurs. Being readily available and a simple procedure, blood sampling would be more reliable and simple to use

What is claimed is:

1. An extension set comprising means defining at least two lumen, one of said lumen being sized to convey an intravenous fluid therethrough and the other of said lumen being sized to convey a drug therethrough; and a common connector receiving each lumen, said connector having means at one end for connecting to a catheter to deliver an intravenous fluid and a drug thereto, a pair of sockets receiving said lumen therein and a partition wall between said sockets and extending to said means at said one end of said connector.

2. In combination,
    a catheter having a needle for implanting into a patient;
    an extension set connected to said catheter, said set including a connector removably secured to said catheter, a first lumen terminating in said connector for delivering an intravenous fluid thereto for passage into said connector and a second lumen terminating in said connector for delivering a drug through said connector into a patient;
    an interfacing chamber within said connector extending from said first and second lumen to said needle, said chamber having a volume to contain no more than two drops of the delivered drug;
    first means connected to a distal end of said first lumen to deliver a flow of intravenous fluid thereto; and
    second means connected to a distal end of said second lumen to deliver a flow of drug thereto.

3. The combination as set forth in claim 2 wherein said second lumen is disposed within said first lumen along a length extending from said connector to a point of separation of said lumen.

4. The combination as set forth in claim 3 wherein said second lumen has an internal diameter of 0.020 inches.

5. The combination as set forth in claim 2 wherein said extension set has an elongated flexible double-tube lumen defining said lumen with said lumen being disposed in side-by-side relation.

6. The combination as set forth in claim 2 which further comprises a hydrophilic filter in a distal end of said second lumen to prevent passage of air into said second lumen.

7. The combination as set forth in claim 3 wherein each lumen is disposed in a tube of a length of from 2 to 4 feet.

8. A method of administering a drug comprising the steps of
    connecting a first lumen of an extension set to a catheter implanted intravenously in a patient to deliver a flow of intravenous fluid to the patient at a predetermined rate over a period of time; and
    introducing a drug at a predetermined rate and dosage for an incremental time through a second lumen of the extension set directly into the patient through said catheter.

9. A method as set forth in claim 8 wherein the drug is interfaced with the fluid flow immediately upstream of the catheter in an interfacing chamber of a volume to contain no more than two drops of the drug.

10. A method as set forth in claim 8 wherein the drug is introduced through the catheter without dilution with the fluid flow.

11. A method as set forth in claim 8 wherein the drug is delivered from a source remote from the catheter.

12. A method as set forth in claim 8 wherein the drug is delivered automatically at spaced-apart intervals of time at said predetermined rate and dosage.

13. A method of clearing an extension set having a pair of lumen disposed in side-by-side relation, a connector receiving a terminal end of each said lumen, a connector at a distal end of one of said lumen for receiving a fluid, and a hydrophilic filter at a distal end of the other of said tubes, said method comprising the steps of
delivering a fluid under pressure to the connector of the one lumen to fill said one lumen and said other lumen in sequential manner through said connector;
venting air from said pair of lumen through said filter at said distal end of said other lumen durihg filling of said pair of lumen with fluid; and
terminating delivery of fluid to said one lumen in response to fluid appearing at said filter in said other lumen.

14. A method as set forth in claim 13 which further comprises the steps of placing a vent cap on the connector to permit venting of air through the cap from the connector during delivering of fluid to said one lumen.

15. In combination,
means defining at least two lumen, one of said lumen being sized to convey an intravenous fluid therethrough and the other of said lumen being movably disposed within said one lumen to project therefrom; and
a common connector receiving each lumen, said connector having means at one end for connecting to a catheter to deliver an intravenous fluid thereto, said other lumen being movably disposed within said connector to project therefrom.

16. An extension set comprising
a double tube lumen, one of said lumen being sized to convey an intravenous fluid therethrough and the other of said lumen being sized to convey a drug therethrough; and
a common male luer connector having a socket receiving said double tube lumen at one end and a bore extending from said socket to an opposite end, said bore being coaxially spaced from said double tube lumen to receive a delivered intravenous fluid and drug therefrom.

17. An extension set as set forht in claim 16 wherein said socket is of greater cross-sectional area than said bore.

18. An extension set as set forth in claim 16 wherein said connector includes an interfacing chamber adjacent a terminal end of each said lumen to interface a conveyed drug with a conveyed intravenous fluid, said chamber having a volume to contain no more than two drops of the delivered drug.

19. An extension set as set forth in claim 16 wherein said lumen each has an internal diameter of 0.020 inches.

20. An extension set as set forth in claim 16 wherein said other lumen is disposed within said one lumen.

21. An extension set as set forth in claim 20 wherein said other lumen is disposed in a tube movably mounted in said one lumen and said connector to project from said connector.

22. An extension set as set forth in claim 16 which further comprises a hydrophilic filter at a distal end of said other lumen to prevent passage of air therethrough into said other lumen.

23. An extension set as set forth in claim 22 which further comprises a removably mounted hydrophobic filter at said distal end of said other lumen to prevent passage of fluid therethrough.

24. An extension set comprising an elongated flexible double-lumen tube having a pair of arms removably secured to each other in side-by-side relation one of said arms being sized to convey an intravenous fluid therethrough and the other of said arms being sized to convey a drug therethrough; a collar slidably mounted about said tube and common connector receiving said tube, said connector having means at one end for connecting to a catheter to deliver an intravenous fluid and a drug thereto.

25. In combination
a catheter for implanting into a patient;
an extension set connected to said catheter, said set including a connector removably secured to said catheter, a first lumen terminating in said connector for delivering an intravenous fluid thereto for passage into said connector and a second lumen terminating in said connector for delivering a drug through said connector into a patient, said second lumen being disposed within said first lumen along a length extending from said connector to a point of separation of said lumen;
first means connected to a distal end of said first lumen to deliver a flow of intravenous fluid thereto; and
a syringe pump connected to a distal end of said second lumen to pump a flow of drug therethrough.

* * * * *

UNITED STATES PATENT AND TRADEMARK OFFICE
CERTIFICATE OF CORRECTION

PATENT NO. : 4,585,435
DATED : April 29, 1986
INVENTOR(S) : VINCENT L. VAILLANCOURT It is certified that error appears in the above-identified patent and that said Letters Patent is hereby corrected as shown below:

```
In the front page, delete "Assignee ... Granville, N.Y."
Column 5, line 53 change "34, and continues" to -35, it continues-
Column 5, line 56 change "develope" to -develop-
Column 5, line 59 change "hydrophobic" to -hydrophilic-
Column 5, line 67 change "intraveneously" to -intravenously-
Column 7, line 4 change "manner similar similar to" to -manner similar to-
Column 7, line 32 change "where were" to -which were-
Column 8, lines 11, 12 change "Tel-" to -Tef-
Column 8, line 12 change "siz" to -six-
Column 11, line 21 change "durihg" to -during-
Column 12, line 1 change "forht" to -forth-
Column 12, line 28 change "relation one of" to -relation, one of-
Column 12, line 32 change "and common" to -and a common-
```

Signed and Sealed this

Fourteenth Day of October, 1986

[SEAL]

Attest:

DONALD J. QUIGG

*Attesting Officer*  *Commissioner of Patents and Trademarks*